(12) United States Patent
Okamoto et al.

(10) Patent No.: US 9,745,241 B2
(45) Date of Patent: Aug. 29, 2017

(54) PRODUCTION METHOD FOR HEXACHLOROACETONE

(71) Applicant: ASAHI GLASS COMPANY, LIMITED, Tokyo (JP)

(72) Inventors: Hidekazu Okamoto, Tokyo (JP); Kouhei Tajima, Tokyo (JP); Tsutomu Naganuma, Tokyo (JP); Tomoyuki Fujita, Tokyo (JP); Shingo Nomura, Tokyo (JP)

(73) Assignee: ASAHI GLASS COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/198,383

(22) Filed: Jun. 30, 2016

(65) Prior Publication Data

US 2016/0304428 A1    Oct. 20, 2016

Related U.S. Application Data

(63) Continuation of application No. PCT/JP2015/050069, filed on Jan. 5, 2015.

(30) Foreign Application Priority Data

Jan. 8, 2014  (JP) ................................. 2014-001698

(51) Int. Cl.
    *C07C 45/63*    (2006.01)
(52) U.S. Cl.
    CPC ................... *C07C 45/63* (2013.01)

(58) Field of Classification Search
    CPC ........................................................ C07C 45/63
    USPC ........................................................ 568/394
    See application file for complete search history.

(56) References Cited

U.S. PATENT DOCUMENTS

| | | | |
|---|---|---|---|
| 2,635,117 | A | 4/1953 | Woolf et al. |
| 3,265,740 | A | 8/1966 | Weinmayr |

FOREIGN PATENT DOCUMENTS

| | | | | |
|---|---|---|---|---|
| GB | 2 082180 | A | | 3/1982 |
| GB | 2082180 | A | * | 3/1982 ............. C07C 45/63 |
| JP | S49-024909 | A | | 3/1974 |
| JP | S56-139436 | A | | 10/1981 |
| JP | S57-035537 | A | | 2/1982 |

OTHER PUBLICATIONS

International Search Report for PCT/JP2015/050069 mailed Apr. 7, 2015.

* cited by examiner

*Primary Examiner* — Sikarl Witherspoon
(74) *Attorney, Agent, or Firm* — Foley & Lardner LLP

(57) ABSTRACT

The present invention relates to a production method of hexachloroacetone, including performing a reaction between at least one kind of compound (A) selected from the group consisting of acetone and chloroacetones having a chlorine atom number of from 1 to 5, and a chlorine molecule (B) in a solvent in the presence of an activated carbon, to obtain the hexachloroacetone.

11 Claims, No Drawings

PRODUCTION METHOD FOR HEXACHLOROACETONE

The present application is a continuation application filed under 35 U.S.C. §111(a) claiming the benefit under 35 U.S.C. §§120 and 365(c) of International Application No. PCT/JP2015/050069 filed on Jan. 5, 2015, which is based upon and claims the benefit of priority of Japanese Patent Application No. 2014-001698 filed on Jan. 8, 2014, the entire contents thereof are incorporated herein by reference.

TECHNICAL FIELD

The present invention relates to a method for producing hexachloroacetone.

BACKGROUND ART

As a production method of hexachloroacetone, for example, the methods described below are known.

(1) Method in which a reaction between acetone and chlorine molecule is performed while using pyridine as a catalyst (Patent Document 1).

(2) Method in which a reaction between acetone and chlorine molecule is performed while using triphenylphosphine as a catalyst (Patent Document 2).

(3) Method in which trichloroacetone and chlorine molecule are supplied to a fixed bed of activated carbon to perform a reaction therebetween by using the activated carbon as a catalyst (Patent Document 3).

However, in the methods of (1) and (2), since the catalyst and its chlorinated product are dissolved in the hexachloroacetone produced by the reaction, it is difficult to recover and further reuse the catalyst and its chlorinated product. Moreover, even when the catalyst and its chlorinated product are removed from the hexachloroacetone by purification (distillation or the like) of a crude product, since small amounts of the catalyst and its chlorinated product remain in the hexachloroacetone, it is difficult to obtain hexachloroacetone of high purity.

According to the method of (3), since chloroacetones having a chlorine atom number of from 1 to 5 are easily condensed, a compound having a high boiling point is apt to be produced. Therefore, in the method of (3), the yield of hexachloroacetone is as low as approximately 80%.

PRIOR ART DOCUMENT

Patent Document

Patent Document 1: U.S. Pat. No. 3,265,740
Patent Document 2: JP-A-56-139436
Patent Document 3: U.S. Pat. No. 2,635,117

SUMMARY OF THE INVENTION

Problems that the Invention is to Solve

The present invention provides a production method in which a catalyst can be easily recovered and which is capable of obtaining hexachloroacetone having a low content of impurities in a high yield.

Means for Solving the Problems

In the production method of hexachloroacetone according to the present invention, a reaction is performed between at least one kind of compound (A) selected from the group consisting of acetone and chloroacetones having a chlorine atom number of from 1 to 5, and a chlorine molecule (B) in a solvent in the presence of an activated carbon, to obtain the hexachloroacetone.

It is preferred that the activated carbon is in a state of being dispersed in the solvent.

It is preferred that the solvent is a compound having no hydrogen atom.

It is preferred that the solvent is hexachloroacetone.

It is preferred that during the reaction between the compound (A) and the chlorine molecule (B), a concentration of the compound (A) in a reaction liquid (excepting for the activated carbon) (100% by mass) is set to 50% by mass or less.

It is preferred that a molar ratio of a total amount of the chlorine molecule (B) supplied as a raw material to a total amount of hydrogen atom in the compound (A) supplied as a raw material ((B)/hydrogen atom in (A)) is 0.83 or more.

Advantage of the Invention

According to the production method of hexachloroacetone of the present invention, a catalyst can be easily recovered and hexachloroacetone having a low content of impurities is able to be obtained in a high yield.

MODE FOR CARRYING OUT THE INVENTION

The definitions of terms described below are applied throughout the present specification and claims.

The term "compound (A)" is a general term for acetone and chloroacetones having a chlorine atom number of from 1 to 5 (monochloroacetone, dichloroacetone, trichloroacetone, tetrachloroacetone, and pentachloroacetone). The compound (A) includes not only a compound (A) supplied as a raw material but also a compound (A) (that is, an intermediate) which is produced by reaction between the compound (A) supplied as the raw material and the chlorine molecule (B) and in which the chlorine atom number is increased from that in the compound (A) supplied as the raw material.

The term "reaction liquid" means a liquid phase among the liquid phase and a gas phase formed in a reactor.

The term "reaction mixture" means a liquid containing hexachloroacetone and activated carbon obtained in step (I) described later, and corresponds to a reaction liquid in which the reaction between the compound (A) and the chlorine molecule (B) proceeds.

<Production Method of Hexachloroacetone>

The production method of hexachloroacetone according to the present invention is a method including performing a reaction between at least one kind of compound (A) selected from the group consisting of acetone and chloroacetones having a chlorine atom number of from 1 to 5, and a chlorine molecule (B) in a solvent in the presence of an activated carbon, to obtain the hexachloroacetone.

As the production method of hexachloroacetone according to the present invention, for example, a method including steps (I) to (III) described below can be exemplified.

(I) Reaction step of performing a reaction between a compound (A) with a chlorine molecule (B) to obtain a reaction mixture containing hexachloroacetone and activated carbon.

(II) Catalyst separation step of separating the activated carbon from the reaction mixture to obtain a crude product.

(III) Purification step of purifying the crude product to obtain hexachloroacetone.

[Step (I)]

The step (I) is a reaction step of performing a reaction between a compound (A) with chlorine molecule (B) in a solvent in the presence of activated carbon to obtain a reaction mixture containing hexachloroacetone and the activated carbon.

(Compound (A))

The compound (A) is at least one kind selected from the group consisting of acetone and chloroacetones having a chlorine atom number of from 1 to 5.

As the compound (A) which is supplied as a raw material, acetone is particularly preferred from the standpoint of easy availability.

Moisture in the compound (A) which is supplied as a raw material is preferably 3% by mass or less, more preferably 1% by mass or less and particularly preferably 0.1% by mass or less, based on 100% by mass of the compound (A) (containing impurities, for example, moisture). Since the moisture reacts with hexachloroacetone, it decreases the yield of hexachloroacetone. Also, in the case of using a reactor made of metal, the moisture causes corrosion of the reactor.

Acetone may contain diacetone alcohol (hereinafter, referred to as DAA) as an impurity. Since DAA becomes a cause of a byproduct in the reaction of the present invention, it is preferred that the amount of DAA is small. Specifically, the amount of DAA is preferably 3% by mass or less and more preferably 1% by mass or less, based on 100% by mass of the acetone (containing impurities, for example, DAA).

(Chlorine Molecule (B))

The chlorine molecule (B) is supplied as a gas containing the chlorine molecule (B) (hereinafter, also referred to as a raw material gas).

The raw material gas may be a gas composed only of the chlorine molecule (B) or may be a mixture of the chlorine molecule (B) and other compound. In the case where a plurality of reactors are disposed in series as described later, hydrogen chloride is included in the raw material gas.

The other compound include a compound capable of reacting with the compound (A) (hydrogen chloride, oxygen molecule, bromine molecule, or the like) and a compound inert to the compound (A) (nitrogen molecule, argon, helium, carbon dioxide, or the like).

The content of hydrogen chloride in the raw material gas is preferably 10% by mass or less and more preferably 5% by mass or less, based on 100% by mass of the raw material gas. Since the hydrogen chloride reacts with the compound (A), it decreases the yield of hexachloroacetone and increases the production amount of impurities.

The content of each of the oxygen molecule and the bromine molecule in the raw material gas is preferably 5% by mass or less and more preferably 1% by mass or less, based on 100% by mass of the raw material gas. Since the oxygen molecule decomposes acetone or the compound (A), it decreases the yield of hexachloroacetone and increases the production amount of impurities. The bromine molecule reacts with acetone or the compound (A) to increase the production amount of impurities including a bromine atom.

The inert compound may be added for the purpose of facilitating control of the reaction or avoiding an explosive reaction between acetone and the chlorine molecule (B).

The content of the inert compound is preferably 50% by volume or less, more preferably 10% by volume or less and particularly preferably 5% by volume or less, based on 100% by volume of the raw material gas. When the content of the inert compound is equal to or less than the upper limit value described above, the volumetric efficiency is excellent.

(Solvent)

The activated carbon is preferably in a state of being dispersed in the solvent. As the solvent, preferred is a solvent which does not substantially react with the chlorine molecule (B), that is, a compound having no hydrogen atom.

As the compound having no hydrogen atom, preferred is carbon tetrachloride, hexachloroacetone, a chlorofluorocarbon, a perfluorocarbon, a perfluoroether, or a chlorofluoroether, and particularly preferred is hexachloroacetone from the standpoint that there is no need to remove the solvent in the step (III).

Moisture in the solvent is preferably 3% by mass or less, more preferably 1% by mass or less and particularly preferably 0.1% by mass or less, based on 100% by mass of the solvent (containing impurities, for example, moisture). Since the moisture reacts with hexachloroacetone, it decreases the yield of hexachloroacetone. Also, in the case of using a reactor made of metal, the moisture causes corrosion of the reactor.

(Catalyst)

In the present invention, the activated carbon is used as a catalyst of the chlorination reaction.

As the kind of the activated carbon, charcoal, coal, coconut shell activated carbon, and the like can be exemplified.

The particle size of the activated carbon is not particularly limited and it is preferred to have a certain size from the standpoint of ease of separation depending on the separation method of activated carbon described later. Specifically, in the case of performing sedimentation separation or separation by cyclone, the average particle size of the activated carbon is preferably 0.1 μm or more and more preferably 1 μm or more. Also, the average particle size of the activated carbon is preferably 5 cm or less. Moreover, the average particle size of the activated carbon is preferably from 10 to 2,000 μm and more preferably from 10 to 500 μm. When the particle size of the activated carbon is equal to or more than the lower limit value described above, the activated carbon is easily separated and it does not take much time for separation. When the particle size of the activated carbon is equal to or less than the upper limit value described above, it is less likely to cause a problem such as clogging of the piping during transport.

The average particle size of the activated carbon is a median diameter measured by a laser diffraction-scattering type measuring device.

Although the catalyst action mechanism with the activated carbon is not sufficiently clarified, it is estimated to have the mechanism described below.

Specifically, there are (i) adsorption step of the compound (A) and the chlorine molecule (B) on a surface of the activated carbon, (ii) chlorination reaction step between the compound (A) and the chlorine molecule (B), adsorbed on the activated carbon, and (iii) desorption step of the compound (A) in which the number of chlorine atoms has been increased by the chlorination, or hexachloroacetone.

From the standpoint of the catalyst action mechanism, it is preferred that the specific surface area of the activated carbon is large. Specifically, the specific surface area of the activated carbon is preferably 10 $m^2/g$ or more, more preferably 100 $m^2/g$ or more and particularly preferably 300 $m^2/g$ or more. Also, the specific surface area of the activated carbon is preferably 5,000 $m^2/g$ or less, more preferably 3,000 $m^2/g$ or less and particularly preferably 2,000 $m^2/g$ or less. Since the activated carbon having a large specific surface area is expensive, it is not preferred from the standpoint of economy.

The specific surface area of the activated carbon can be obtained according to an analysis by a BET method using nitrogen gas at −195.8° C.

It is preferred that the activated carbon is sufficiently dried before using in the reaction. Specifically, moisture in the activated carbon before the use is preferably 10% by mass or less, more preferably 5% by mass or less and particularly preferably 1% by mass or less, based on 100% by mass of the activated carbon (containing moisture). Since the moisture reacts with hexachloroacetone, it decreases the yield of hexachloroacetone. Also, in the case of using a reactor made of metal, the moisture causes corrosion of the reactor.

(Reaction Equipment)

The reaction in the present invention is a reaction in a mixed state of gas and liquid and is preferred to be performed in a state in which the gas and liquid are sufficiently mixed. The state can be achieved, for example, by using a reactor equipped with a stirrer, a tubular reactor, a plate column type reactor, or the like. Moreover, for the purpose of sufficiently mixing the gas and liquid, it is also effective to install a plurality of supply ports for the chlorine molecule (B) to the reactor.

In the step (I), the chlorine molecule (B) is used, hydrogen chloride is generated, and the reaction temperature is high. Thus, a material of the reactor used in the step (I) is required to be a material which is resistant to the chlorine molecule (B) and hydrogen chloride and can be used at a high temperature. As the material, there can be exemplified alumina, zirconia or the like as a metal oxide, nickel, Hastelloy, Monel, or the like as a metal or alloy, polytetrafluoroethylene, a tetrafluoroethylene-perfluoro(alkylvinylether) copolymer, an ethylene-tetrafluoroethylene copolymer, or the like as a plastic, glass, and carbon. Moreover, those obtained by coating or lining the material described above on other material can also be used.

(Reaction System)

The reaction system may be a batch system or a continuous system.

In the case of performing the reaction by the batch system, there can be exemplified (i) a method of adding the chlorine molecule (B) to an activated carbon dispersion in which the compound (A) is dissolved, (ii) a method of simultaneously supplying the compound (A) and the chlorine molecule (B) to an activated carbon dispersion, and the like. The method of (ii) is preferred from the standpoint that the side reaction can be suppressed as described later because the concentration of the compound (A) can be lowered and that, since the compound (A) is converted to hexachloroacetone which is the solvent, the initial solvent content can be decreased and thereby the volumetric efficiency can be improved.

In the case of performing the reaction by the continuous system, there can be exemplified a reaction method using CSTR (continuous tank reactor) (hereinafter, referred to as a CSTR type reaction method), a reaction method using a plug flow reactor (tubular reactor) (hereinafter, referred to as a PFR type reaction method), a method in which these are combined, and the like.

The CSTR type reaction method is a method in which the activated carbon, solvent, compound (A), and chlorine molecule (B) are continuously supplied to a reactor equipped with a stirrer, and a reaction mixture is continuously taken out from the reactor.

The PFR type reaction method is (i) a method of contentiously supplying the activated carbon, solvent, compound (A) and chlorine molecule (B) to a tubular reactor, or (ii) a method of filling the activated carbon in a tubular reactor and continuously supplying thereto the solvent, compound (A) and chlorine molecule (B). In either case, a reaction mixture is continuously taken out at a point at a certain distance, in the flow direction, from a point where the activated carbon, solvent, compound (A), and chlorine molecule (B) have been supplied. As the tubular reactor, there can be exemplified one having end points as a straight tube type and one having no end point as a circular tube type (loop type).

In the case of the CSTR type reaction method, since the reaction is carried out under stirring, the composition is equivalent at the supply point and at the taking out point, but in the case of the PFR type reaction method, the composition is different between the supply point and the taking out point.

Even when any reaction method is selected, when the desired conversion rate cannot be achieved by one reactor, a reaction for the purpose of increasing the conversion rate to hexachloroacetone can be further performed by the same or different reactor. In particular, in the case of selecting the CSTR type reaction method, the conversion rate of the compound (A) and the chlorine molecule (B) can be highly maintained by using two or more reactors. That is, in the case of using two reactors, the two reactors are connected in series, the compound (A) is supplied to the first reactor, the chlorine molecule (B) is supplied to the second reactor, the liquid of the first reactor is supplied to the second reactor, and the outlet gas of the second reactor is supplied to the first reactor, whereby the conversion rate of the compound (A) and the chlorine molecule (B) can be highly maintained.

(Reaction Conditions)

During the reaction between the compound (A) and the chlorine molecule (B), the concentration of the compound (A) in the reaction liquid (excepting for the activated carbon) (100% by mass) is preferably set to 50% by mass or less and more preferably set to 20% by mass or less. As described later, as the concentration of the compound (A) decreases, a side reaction can be suppressed.

The concentration of the compound (A) in the reaction liquid can be analyzed by gas chromatography.

The concentration of the compound (A) in the reaction liquid can be adjusted by an amount of the solvent, supply rates of the compound (A) and the chlorine molecule (B), a reaction rate, or the like. The reaction rate can be adjusted by temperature, an amount of the catalyst or the like. That is, when the concentration of the compound (A) is high, the concentration of the compound (A) can be reduced by an additional supply of the solvent, a decrease in the supply rate of the raw material, an increase in the reaction temperature, or an increase in the concentration of the activated carbon.

A molar ratio of the chlorine molecule (B) to a hydrogen atom in the compound (A) ((B)/hydrogen atom in (A)) which is theoretically required in the reaction according to the present invention is 1. In the case where the ((B)/hydrogen atom in (A)) is too small, the concentration of compound (A) is increased to decrease the purity of hexachloroacetone. Therefore, in order to enhance the conversion rate to hexachloroacetone, a molar ratio of a total amount of the chlorine molecule (B) supplied as a raw material to a total amount of hydrogen atom in the compound (A) supplied as a raw material, that is, a charged molar ratio of the chlorine molecule (B) to a hydrogen atom in the compound (A) ((B)/hydrogen atom in (A)) is preferably 0.83 or more and more preferably 0.92 or more. On the other hand, in the case where the chlorine molecule (B) is excessively used, the excess chlorine molecule (B) can be recovered but the efficiency of the overall process is low. Therefore, the charged molar ratio of the chlorine molecule (B) to a hydrogen atom in the compound (A) ((B)/hydrogen atom in (A)) is preferably 1.67 or less, more preferably 1.33 or less and particularly preferably 1.02 or less.

The concentration of the activated carbon is preferably from 0.05 to 30% by mass and more preferably from 0.1 to 20% by mass, based on the reaction liquid (containing the activated carbon) (100% by mass). When the concentration of the activated carbon is equal to or more than the lower limit value described above, the reaction rate is high and the productivity is good. On the other hand, even when a large amount of the activated carbon is used, since the activated carbon can be reused, there is no limitation to the amount of the activated carbon from the standpoint of waste amount. However, the concentration of the activated carbon exceeds the upper limit value described above, the power for dispersing the activated carbon in the reaction liquid becomes great and the volumetric efficiency of the reactor is deteriorated.

The reaction temperature is preferably from 80 to 250° C. and more preferably from 100 to 200° C. When the reaction temperature is equal to or more than the lower limit value described above, the reaction rate becomes high and the productivity is enhanced. On the other hand, since a boiling point of the hexachloroacetone at a normal pressure is 204° C. and a boiling point of the compound (A) is equal to or less than that, when the reaction temperature is raised too high, loss of the hexachloroacetone and compound (A) to the outside of the reactor increases and the load of facilities for recovering the hexachloroacetone and compound (A) volatilized becomes large. Therefore, to raise the temperature too much is not preferred.

The reaction pressure (gauge pressure) is preferably from 0 to 5 MPaG, more preferably from 0.1 to 5 MPaG and particularly preferably from 0.1 to 1 MPaG. When the reaction pressure is equal to or more than the lower limit value described above, since the vapor pressures of the compound (A) and hexachloroacetone are decreased, the capacity of condenser or the like for recovering them can be suppressed so that the investment can be reduced. On the other hand, in order to increase the reaction pressure, it is necessary to use a pressure resistant reactor and since too high pressure causes increase in the investment for the reactor, it is not preferred that the reaction pressure is too high.

In the case of the batch system, by prolonging the reaction time, the concentration of the compound (A) in the reaction liquid is decreased and as a result, the purity of hexachloroacetone is increased. On the other hand, too long reaction time is not preferred from the standpoint of productivity. Moreover, hexachloroacetone can also be purified in the step (III) and it is not always necessary to be made highly purified at the stage of step (I). Therefore, the reaction time is preferably approximately from 1 to 24 hours.

In the case of the continuous system, a retention time (min), which is a ratio of the taking out rate (L/min) of the reaction mixture to the volume (L) of the reaction liquid, corresponds to the reaction time. By prolonging the retention time, the purity of hexachloroacetone can be highly maintained. On the other hand, too long retention time is not preferred from the standpoint of productivity. Moreover, the retention time required also depends on the reaction temperature and the amount of activated carbon used and is varied by the conditions of the entire process including the step (III). Putting together these, the retention time is preferably from 5 to 5,000 minutes and more preferably from 10 to 1,000 minutes.

In the case where the reaction temperature is high, since hexachloroacetone and the compound (A) are volatized together with the gas, it is preferred to recover hexachloroacetone and the compound (A) from the gas. As the method of recovering hexachloroacetone and the compound (A) in the gas, there can be exemplified a method of cooling by a condenser or the like, a method of absorbing hexachloroacetone and the compound (A) in the gas by an absorption tower using a solvent which does not substantially react with the chlorine molecule (B), a method in which these are combined, and the like.

(Hydrogen Chloride)

In the step (I), hydrogen chloride gas is generated together with hexachloroacetone. Also, in the case of using excessively the chlorine molecule (B), the chlorine molecule (B) may be included in the hydrogen chloride gas. The hydrogen chloride gas or a mixed gas of the hydrogen chloride and the chlorine molecule (B) may be treated by a neutralization reaction with a metal hydroxide, a metal oxide, a metal carbonate, or an aqueous solution thereof, or may be effectively utilized by other methods. The hydrogen chloride gas can be used in the production of chloromethane by chlorination of methanol or in the production of vinyl chloride by an oxychlorination reaction with ethylene and also it can be converted to chlorine by a reaction with oxygen. Also, an aqueous solution of hydrogen chloride can also be used as hydrochloric acid. In the case where the hydrogen chloride gas is required to be purified in higher purity in order to be used for these applications, purification may be performed. As the purification method, there can be exemplified distillation, washing with water and other solvents, washing with concentrated hydrochloric acid or sulfuric acid, removal of the chlorine molecule (B) or an organic substance with activated carbon, and the like, and a combination thereof may be performed.

[Step (II)]

The step (II) is a catalyst separation step of separating the activated carbon from the reaction mixture obtained in the step (I), to obtain a crude product.

In the step (I), hexachloroacetone is obtained in the state of being mixed with the activated carbon. In the case where the hexachloroacetone obtained in the step (I) is used as the solvent of the step (I), the reaction mixture may be used as it is. In the case where the hexachloroacetone obtained in the step (I) is used in other applications, it is preferred to separate the activated carbon from the reaction mixture.

The step (II) may be performed by any method as long as the activated carbon can be separated and it can be performed by various conventional methods which are used for separating solid and liquid. As the separation method, for example, filtration, sedimentation, centrifugation, distillation, and the like can be exemplified. The separation method may be a batch system or a continuous system.

The step (II) may be performed in the state where the reaction mixture is still hot or may be performed after cooling the reaction mixture. The step (II) is preferably performed in the state where the reaction mixture is still hot from the standpoint of energy efficiency, and it is preferably performed after cooling the reaction mixture from the standpoint of suppressing the influence on the material of the equipment used and the generation of cavitation or the like which occurs during the operation. In the case of performing sedimentation or centrifugation, it is preferably performed in the state where the reaction mixture is still hot because it is advantageous that the difference in specific gravity between the activated carbon and hexachloroacetone is large. The temperature is preferably from 80 to 200° C. from the standpoint that the boiling point of hexachloroacetone is 204° C., and for heating to the temperature higher than that, an equipment which is resistant to pressure is required and the energy for performing the heating and heat retention is required.

The pressure (gauge pressure) in the step (II) is appropriately selected depending on the separation method and is preferably from −0.1 to 1.0 MPaG.

The material of the equipment used in the step (II) is required to be a material which is resistant to the chlorine molecule (B) and hydrogen chloride and is stable thermally and chemically at the temperature to be used.

In the case in which the step (II) is performed in the state where the reaction mixture is still hot, as the material, there can be exemplified alumina, zirconia or the like as a metal oxide, nickel, Hastelloy, Monel, or the like as a metal or alloy, polytetrafluoroethylene, a tetrafluoroethylene-perfluoro(alkylvinylether) copolymer, an ethylene-tetrafluoroethylene copolymer, or the like as a plastic, glass, and carbon. Moreover, those obtained by coating or lining the material described above on other material can also be used.

In the case in which the step (II) is performed after cooling the reaction mixture, as the material, a plastic (polyethylene, polypropylene, polyvinyl chloride, chlorinated polyvinyl chloride, or the like) can be additionally exemplified.

The activated carbon separated is preferably reused in the step (I). The activated carbon separated is usually obtained as a mixture containing hexachloroacetone, the compound (A) and the like (hereinafter, referred to as an activated carbon mixture). The solid content concentration of the activated carbon mixture may vary depending on the separation method of activated carbon and is usually from 5 to 99% by mass.

The activated carbon mixture may be charged to the reactor in the step (I) as it is, or may be charged to the reactor after performing an appropriate adjustment of the solid content concentration because the activated carbon mixture containing no liquid component at all is disadvantageous for the transfer or the like in some cases.

As the liquid used for the adjustment of the solid content concentration of the activated carbon mixture, there can be exemplified carbon tetrachloride, hexachloroacetone, a chlorofluorocarbon, a perfluorocarbon, a perfluoroether, the compound (A), a mixture thereof, and the like, and preferred are hexachloroacetone, the compound (A) and a mixture thereof.

The solid content concentration of the activated carbon mixture after the adjustment is preferably from 2 to 50% by mass and more preferably from 10 to 30% by mass. When the activated carbon mixture has the solid content concentration of equal to or more than the lower limit value described above, it does not deteriorate the volumetric efficiency when it is returned to the reactor. When the activated carbon mixture has the solid content concentration of equal to or less than the upper limit value described above, the power for the transfer is small and a problem such as clogging of the piping does not occur.

The activated carbon can be repeatedly used plural times. In the case where the activated carbon is deteriorated for some reason, it is appropriately discarded. When the activated carbon is discarded, it is preferred to recover hexachloroacetone from the activated carbon mixture. As the recovery method, there can be exemplified a method of filtering the activated carbon mixture by a method capable of recovering the liquid component (filter press or the like), a method of recovering hexachloroacetone as being vaporized by heating the activated carbon mixture, and the like.

[Step (III)]

The step (III) is a purification step of purifying the crude product obtained in the step (II) to obtain hexachloroacetone.

In the step (II), hexachloroacetone is obtained in the state of being mixed with the compound (A), the chlorine molecule (B), hydrogen chloride, and the like. In the case where the hexachloroacetone is used for the application which allows containing other components, the crude product may be used as it is for the application. In the case where it is used for the application which requires high purity hexachloroacetone, it is preferred to be appropriately purified depending on the required purity.

As the purification method, washing with water, sodium bicarbonate water or the like, distillation, recrystallization, and the like are exemplified, and distillation is preferred.

The distillation can be performed by a conventional method. The distillation may be a batch system or may be a continuous system and is preferably a continuous system from the standpoint of productivity.

It is preferred to separate the chlorine molecule (B) and hydrogen chloride before performing the distillation from the standpoint of reduction in the equipment corrosion. The chlorine molecule (B) and hydrogen chloride are easily separated by heating or reducing pressure. Also, they can be sufficiently reduced by passing gas, for example, nitrogen gas or helium gas therethrough.

The material of the distillation facility or the like is required to be a material which is resistant to the chlorine molecule (B) and hydrogen chloride and can be used at a high temperature. As the material, there can be exemplified alumina, zirconia or the like as a metal oxide, nickel, Hastelloy, Monel, or the like as a metal or alloy, polytetrafluoroethylene, a tetrafluoroethylene-perfluoro(alkylvinylether) copolymer, an ethylene-tetrafluoroethylene copolymer, or the like as a plastic, glass, and carbon. Moreover, those obtained by coating or lining the material described above on other material can also be used.

[Mechanism of Action]

In the production method of hexachloroacetone according to the present invention described above, since the hexachloroacetone is obtained by a reaction between the compound (A) and the chlorine molecule (B) in a solvent in the presence of activated carbon, the hexachloroacetone having a small amount of impurities can be obtained in a high yield for the reason described below.

In the reaction between the compound (A) and the chlorine molecule (B), since the compound (A) is unstable, the compounds (A) are condensed with each other to be likely to generate a compound having a high boiling point. That is, it is believed that in the case of using no solvent, the state in which the concentration of the compound (A) is high is caused to generate a condition in which the condensation reaction is apt to occur, whereby the compound having a high boiling point is increased. On the other hand, it is believed that in the case of using a solvent, the concentration of the compound (A) can be suppressed to a low level to generate a condition in which the condensation reaction is difficult to occur, whereby the compound having a high boiling point is hard to be produced.

Also, in the production method of hexachloroacetone according to the present invention described above, since the activated carbon is used as a catalyst, the catalyst can be easily recovered. As a result, the catalyst can be repeatedly used so that the method is economically advantageous and also the amount of the waste can be reduced.

Moreover, in the case of using hexachloroacetone as the solvent, it is not necessary to perform the separation of the solvent so that the productivity is good.

EXAMPLES

Hereinafter, the present invention will be described in detail with reference to the Examples, but the present invention is not limited thereto.

Example 1

To a reactor made of nickel having an inner volume of 3 L equipped with a condenser was charged 36.1 g of powdered activated carbon (powdered SHIRASAGI activated carbon, average particle size: 45 μm, specific surface area: 876 m$^2$/g, produced by Japan EnviroChemicals, Ltd.) which had been dried, followed by supplying chlorine molecule (B) at 0.3 L/min for one hour. To the reactor was charged 1,750 g of hexachloroacetone (produced by Aldrich Co.) as a solvent, followed by initiating stirring, and raising the internal temperature to 150° C. The chlorine molecule (B) was supplied at 10.6 mol/hour. After 5 minutes from the initiation of the supply of chlorine molecule (B), acetone was supplied at 1.3 mol/hour, and a heating was gradually performed so as to maintain the temperature from 150° C. to 155° C. After 300 minutes from the initiation of the supply of acetone, the supply of acetone was terminated. The flow rate of the chlorine molecule (B) was changed to 5.3 mol/hour and the reaction was further continued for one hour. In total, 394 g (6.79 mol) of the acetone and 4,496 g (63.41 mol) of the chlorine molecule (B) were supplied and the charged molar ratio of the chlorine molecule (B) to a hydrogen atom in the acetone ((B)/hydrogen atom in acetone) was 1.56.

The gas discharged from the reactor was passed through an absorption tower that was cooled to 0° C. and contained 634 g of hexachloroacetone as an absorption liquid, a cold trap at −20° C., and an about 20% by mass aqueous sodium hydroxide solution. In this manner, an organic substance, for example, hexachloroacetone or the compound (A) was recovered by the absorption tower and the cold trap, and the chlorine molecule (B) and hydrogen chloride were absorbed by the aqueous sodium hydroxide solution.

As a result of analysis of the reaction mixture liquid in the reactor by gas chromatography by using an internal standard, the yield of hexachloroacetone produced by the reaction was 94% and the total yield of chloroacetones having a chlorine atom number of from 1 to 6 was 99%. The reaction mixture liquid obtained was filtered through a polytetrafluoroethylene-made filter having a pore size of 0.2 μm to obtain a crude product. As a result of distilling the crude product, a compound having a high boiling point was confirmed 0.4% by mass with respect to the crude product. The results are shown in Table 2.

Examples 2 to 4

The same operations as in Example 1 were performed except for changing the reaction conditions as shown in Table 1 and Table 2. The results are shown in Table 2.

TABLE 1

| | Overall Conditions | | | | Conditions at Acetone Supply | | | Conditions after Completion of Acetone Supply | |
|---|---|---|---|---|---|---|---|---|---|
| | Initial | | | | | Flow Rate | | | |
| Example | Solvent (HCA) g | Activated Carbon g | Reaction Temperature ° C. | Reaction Pressure MPaG | Acetone g | Flow Rate of Acetone mol/hour | Flow Rate of Cl$_2$ mol/hour | Flow Rate of HCl mol/hour | Flow Rate of Cl$_2$ mol/hour | Reaction Time hour |
| 1 | 1,750 | 36.1 | 155 | 0 | 394 | 1.3 | 10.6 | 0 | 5.3 | 1 |
| 2 | 1,750 | 102.0 | 110 | 0 | 378 | 1.3 | 10.6 | 0 | 5.3 | 0 |
| 3 | 1,750 | 35.4 | 155 | 0.3 | 388 | 1.3 | 8.0 | 0 | 4.0 | 1 |
| 4 | 1,750 | 36.6 | 155 | 0.3 | 386 | 1.3 | 6.7 | 1.3 | 3.3 | 2 |

HCA: Hexachloroacetone

TABLE 2

| | In Reaction Liquid | | Charge | | | Yield | | |
|---|---|---|---|---|---|---|---|---|
| Example | Concentration of Compound (A) % by mass | Concentration of Activated Carbon % by mass | Acetone g | Cl$_2$ g | (B)/Hydrogen Atom in Acetone molar ratio | HCA % | Total of Cl$_{1-6}$ Chloroacetones % | Compound Having High Boiling Point % |
| 1 | 0.4 | 2.0 | 394 | 4,496 | 1.56 | 94 | 99 | 0.4 |
| 2 | 3.3 | 5.5 | 378 | 4,458 | 1.61 | 91 | 97 | 0.4 |
| 3 | 1.1 | 2.0 | 388 | 3,332 | 1.17 | 95 | 96 | 0.8 |
| 4 | 7.8 | 2.0 | 386 | 2,896 | 1.02 | 92 | 95 | 5.5 |

HCA: Hexachloroacetone

Example 5

The influence in the case of reusing the activated carbon was investigated in the manner described below.

To a reactor made of nickel having an inner volume of 3 L equipped with a condenser was charged 16.6 g of the same powdered activated carbon as in Example 1 which had been dried, followed by supplying chlorine molecule (B) at 0.3 L/min for 30 minutes. To the reactor was charged 1,499 g of hexachloroacetone (produced by Aldrich Co.) as a solvent, followed by initiating stirring, and raising the internal temperature to 150° C. The chlorine molecule (B) was supplied at 4 L/min, and the internal pressure was set to 0.3 MPaG. After 5 minutes from the initiation of the supply of chlorine molecule (B), acetone was supplied at 0.023 mol/min, and the heating was gradually performed so as to maintain the temperature from 150° C. to 160° C. At the time, a molar flow rate ratio of the chlorine molecule (B) and acetone was 7.7. After 6 hours from the initiation of the supply of acetone, the supply of acetone was terminated. At the time, as to the composition of the reaction liquid, hexachloroacetone was 97.2% by mass, pentachloroacetone was 2.0% by mass and other chloroacetone was 0.8% by mass. The flow rate of the chlorine molecule (B) was changed to 2 L/min and the reaction was further continued for one hour. In total, 448.0 g (7.71 mol) of the acetone and 4,779 g (67.4 mol) of the chlorine molecule (B) were supplied.

The gas discharged from the reactor was passed through an absorption tower that was cooled to 0° C. and contained 629.1 g of hexachloroacetone as an absorption liquid, a cold trap at −20° C. and an about 20% by mass aqueous sodium hydroxide solution. In this manner, an organic substance, for example, hexachloroacetone or the compound (A) was recovered by the absorption tower and the cold trap, and the chlorine molecule (B) and hydrogen chloride were absorbed by the aqueous sodium hydroxide solution.

After the completion of the reaction, the stirring was terminated while maintaining the temperature of the reaction mixture liquid to sediment the activated carbon, followed by taking out 1,703 g of the supernatant liquid through the insert tube. When the liquid taken out was analyzed by gas chromatography, it was found that 99.9% by mole was hexachloroacetone. At the time, it is estimated that 1,740 g of hexachloroacetone and 16.6 g of the activated carbon remain in the reactor. By using the remaining hexachloroacetone as the solvent and the remaining activated carbon as the catalyst, the chlorine molecule (B) and acetone were continuously added in the same manner as in the first time. After repeating the operation three times in total, the hexachloroacetone and activated carbon remaining in the reactor were also recovered.

The acetone supplied in the four operations described above was 1,779 g (30.6 mol) in total, and the total of the supernatant liquid and the organic substance absorbed by the absorption liquid, which were recovered, was 9,566 g. From the analysis of the supernatant liquid and the absorption liquid recovered in each batch, it was found that the yield of hexachloroacetone was 98.4%, the yield of 1,1,1-trichloroacetone was 0.5% and the yield of other chloroacetones was 0.7% with respect to the acetone supplied, and the hexachloroacetone could be obtained in a very high yield. Also, the decrease in catalyst activity associated with the reuse of activated carbon was not found.

The supernatant liquid recovered in each batch, and the hexachloroacetone and activated carbon remaining in the reactor were filtered through a polytetrafluoroethylene-made filter having a pore size of 0.2 μm to obtain a crude product. As a result of distilling the crude product, 1.0% by mass of a compound having a high boiling point with respect to the crude product was confirmed.

INDUSTRIAL APPLICABILITY

By a reaction of the hexachloroacetone obtained by the production method according to the present invention with an alcohol, various carbonates and chloroform can be produced. Also, by a liquid phase fluorination reaction of the hexachloroacetone, hexafluoroacetone can be produced. Moreover, the hexachloroacetone is suitable as a solvent for a chlorination reaction with chlorine molecule, and can also be used as a solvent for the chlorination reaction of a compound other than acetone.

While the present invention has been described in detail and with reference to specific embodiments thereof, it will be apparent to one skilled in the art that various changes and modifications can be made therein without departing from the spirit and scope of the present invention.

The invention claimed is:

1. A production method of hexachloroacetone, comprising performing a reaction between at least one kind of compound (A) selected from the group consisting of acetone and chloroacetones having a chlorine atom number of from 1 to 5, and a chlorine molecule (B) in a solvent in the presence of an activated carbon, to obtain the hexachloroacetone.

2. The production method of hexachloroacetone according to claim 1, wherein the activated carbon is in a state of being dispersed in the solvent.

3. The production method of hexachloroacetone according to claim 1, wherein the solvent is a compound having no hydrogen atom.

4. The production method of hexachloroacetone according to claim 1, wherein the solvent is hexachloroacetone.

5. The production method of hexachloroacetone according to claim 1, wherein during the reaction between the compound (A) and the chlorine molecule (B), a concentration of the compound (A) in a reaction liquid (excepting for the activated carbon) (100% by mass) is set to 50% by mass or less.

6. The production method of hexachloroacetone according to claim 1, wherein a molar ratio of a total amount of the chlorine molecule (B) supplied as a raw material to a total amount of hydrogen atom in the compound (A) supplied as a raw material ((B)/hydrogen atom in (A)) is 0.83 or more.

7. The production method of hexachloroacetone according to claim 1, wherein an amount of diacetone alcohol (DAA) in the acetone is 3% by mass or less.

8. The production method of hexachloroacetone according to claim 1, wherein a content of hydrogen chloride in the raw material gas is 10% by mass or less.

9. The production method of hexachloroacetone according to claim 1, wherein the content of each of an oxygen molecule and a bromine molecule in the raw material gas is 5% by mass or less.

10. The production method of hexachloroacetone according to claim 1, wherein the compound (A) is acetone.

11. The production method of hexachloroacetone according to claim 1, wherein a molar ratio of the chlorine molecule (B) to a hydrogen atom in the compound (A) ((B)/hydrogen atom in (A)) is 1.67 or less.

* * * * *